United States Patent [19]

Tanaka

[11] 4,366,206
[45] Dec. 28, 1982

[54] NOVEL WATER-SWELLABLE FIBERS HAVING A HIGH DEGREE OF WATER-SWELLABILITY AND EXCELLENT PHYSICAL PROPERTIES AND PROCESS FOR PRODUCING THE SAME

[75] Inventor: Koji Tanaka, Okayama, Japan
[73] Assignee: Japan Exlan Co., Ltd., Osaka, Japan
[21] Appl. No.: 295,314
[22] Filed: Aug. 24, 1981

Related U.S. Application Data

[63] Continuation of Ser. No. 30,872, Apr. 17, 1979, abandoned.

[30] Foreign Application Priority Data

Apr. 18, 1978 [JP] Japan .................................. 53-46058

[51] Int. Cl.³ ............................................. D02G 3/00
[52] U.S. Cl. .................................... 428/373; 8/115.5; 428/364; 428/374; 428/400
[58] Field of Search .............. 428/364, 373, 374, 400, 428/375; 8/115.5; 264/182, 206

[56] References Cited

U.S. PATENT DOCUMENTS

| | | | |
|---|---|---|---|
| 2,749,330 | 6/1956 | Banes et al. ......................... | 525/336 |
| 3,460,897 | 8/1969 | Lowes, Jr. ........................... | 8/115.5 |
| 3,728,072 | 4/1973 | Orito et al. ......................... | 428/400 |
| 3,929,946 | 12/1975 | Orito et al. ......................... | 428/400 |
| 4,143,200 | 3/1979 | Radlmann et al. .................. | 428/373 |

*Primary Examiner*—Lorraine T. Kendell
*Attorney, Agent, or Firm*—Wenderoth, Lind & Ponack

[57] ABSTRACT

Novel water-swellable fibers having a multiple layer structure consisting of an hydrogel outer layer and an inner layer of an acrylonitrile polymer and/or another polymer, which combine a high degree of water-swellability with excellent physical properties, and a process for producing the same.

10 Claims, 1 Drawing Figure

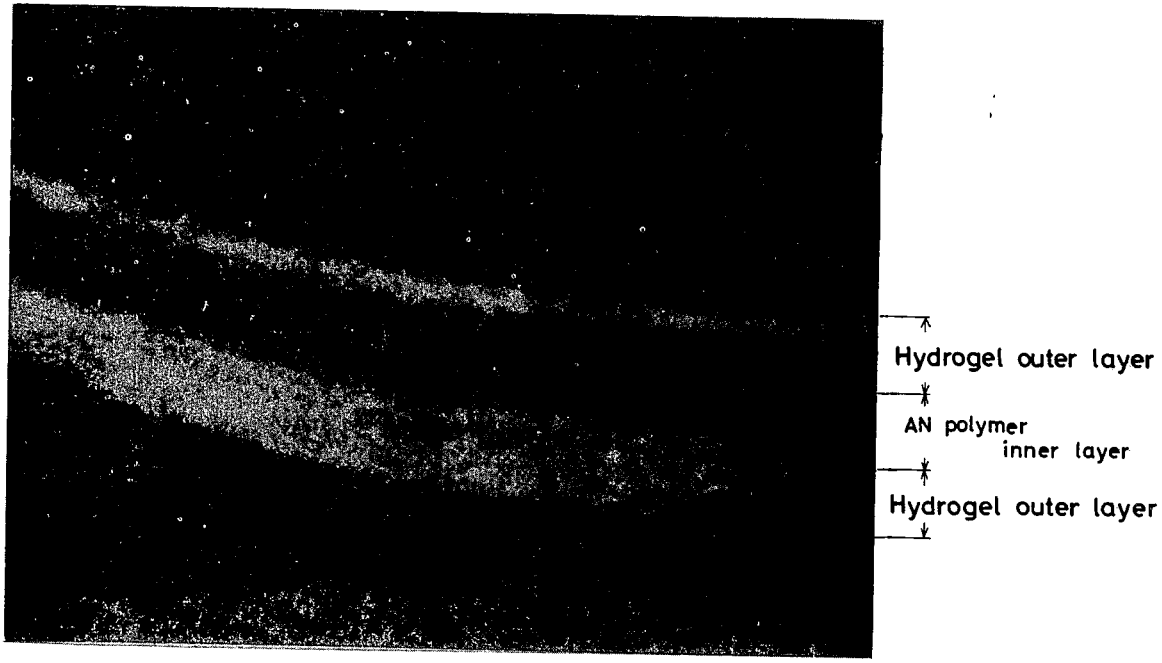

NOVEL WATER-SWELLABLE FIBERS HAVING A HIGH DEGREE OF WATER-SWELLABILITY AND EXCELLENT PHYSICAL PROPERTIES AND PROCESS FOR PRODUCING THE SAME

CROSS-REFERENCE TO PRIOR APPLICATION

This is a continuation of Application Ser. No. 30,872, filed Apr. 17, 1979, and now abandoned.

BACKGROUND OF THE INVENTION

1. Field of the Invention

The present invention relates to novel water-swellable fibers having a multiple layer structure consisting of an outer layer of a hydrophilic cross-linked polymer (hereinafter abbreviated as hydrogel) and an inner layer of an acrylonitrile polymer (hereinafter abbreviated as AN polymer) and/or another polymer, and to a process for producing the same.

2. Description of the Prior Art

In recent years, polymers having a high degree of water-swellability are used in a wide field of applications because of their particular functions. For example, attempts are made on applications to drapers, sanitary products, etc. by utilizing the instantaneous high water-absorbing power of these polymers; or applications to soil-improving materials, instant sandbags, etc. by utilizing their high water-retentive capacity; or applications to soft contact lenses, artificial internal organs, surgical seaming materials, etc. on account of their intimate affinity to human tissues, and among these applications some are already entering on a practical stage.

As regards the water-swellable polymers (hydrogels) having possibilities of use in such a wide field of applications, cases are not few where it is preferable that they take the form of fibers to meet their use purposes, and several hydrogels in the form of fibers are known. However, although such existing natural or synthetic fibers have a certain extent of water-swellability, some have an extremely low water-swellability and others are water-soluble, and in any case they have been far from the category of water-swellable fibers which can absorb and retain an amount of water several to several hundred times their own weight, and moreover are water-insoluble. In Japanese Laid-Open (Kokai) Patent Application No. 42916/1977, there is disclosed a highly swellable fiber-shaped structure composed of arcylic fibers into which specific cross-linkages and a large amount of salt-form carboxyl groups have been introduced. However, since this fiber-shaped structure contains an extremely large amount of salt-form carboxyl groups introduced thereinto and is hydrogelled throughout the outer and inner layers of the fibers, it is provided, on the one hand, with a high degree of water-swellability indeed, but on the other hand, it is so brittle that its physical properties are far from the conception of fibers. That is to say, it is the present situation that there are no water-swellable fibers having satisfactory properties, and thus the giving of a high degree of water-swellability and the retention of fiber physical properties have been a contradictory problem.

STATEMENT OF THE INVENTION

In such a situation, we have researched intensively to overcome the above-mentioned fundamental difficulty and to give a high degree of water-swellabilty to fibers while retaining the physical properties of the fibers. As a result, it has been found that, when an aqueous solution of a specific alkali-metal hydroxide is caused to act on fibers composed of an AN polymer (hereinafter abbreviated as AN fibers) in such a way that only the outer layer of the fibers is selectively rendered hydrophilic and cross-linked (hydrogelled), a high degree of water-swellability can be advantageously given to the fibers, without impairing the fiber physical properties. The present invention is based on this discovery.

Therefore, the object of the present invention is to provide novel water-swellable fibers possessing both a high degree of water-swellability and excellent physical properties and to provide a process for producing such fibers.

The water-swellable fibers according to the present invention to attain the above-mentioned object are composed of a hydrogel outer layer and an inner layer of an AN polymer and/or another polymer. Such water-swellable fibers can be advantageously produced when an aqueous solution of an alkali-metal hydroxide of a high concentration not less than 6.0 mol/1000 g or an aqueous solution of an alkali-metal hydroxide of a low concentration coexisting with an electrolytic salt of a concentration not less than 0.5 mol/1000 g is caused to act on AN fibers to hydrogel the outer layer of said fibers in such a way that the fibers will be composed of a hydrogel outer layer and an inner layer of an AN polymer and/or another polymer.

The invention will be explained in more detail in the following description which will be made by referring partly to the FIG. 1 which is an optical microscopic photograph of an example of the water-swellable fibers (the degree of water-swellability 12 times) of the present invention in a water-swollen state.

DESCRIPTION OF PREFERRED EMBODIMENTS

As used in the present invention the term "AN polymers" is a generic term for polymers containing AN as a copolymerization component, and include AN homopolymers; copolymers of AN with one or more ethylenically unsaturated compounds; graft copolymers of AN with other polymers such as starch, polyvinyl alcohol, etc.; and mixed polymers composed of AN polymers and other polymers such as polyvinyl chloride, polyamides, polyolefins, polystyrenes, polyvinyl alcohols, cellulose, etc. The content of AN in such an AN polymer is desirably not less than 30 wt. %, and more preferably not less than 50 weight %. If fibers from a polymer having an AN content less than the above-recommended limit are used as the starting material, the fibers will not be made sufficiently hydrophilic by the alkaline hydrolytic treatment, or even if made hydrophilic, the fibers will not become water-swellable. There are no particular restrictions on the kind of the above-mentioned ethylenically unsaturated compounds which are copolymerization components of the AN polymers, and on the molecular weight of said polymers, and these can be selected voluntarily to meet the demanded properties of the final product, copolymerizability of the monomer, etc. Also, as regards the process for producing the polymers and the process for forming fibers from the polymers, these can be selected voluntarily from known processes (for example, mono-component spinning, sheath-core composite spinning, etc.). From the viewpoint of industrial production, it is preferable to use mono-component fibers of an AN polymer, but there may be used sheath-core type fibers, of which the sheath component is made of an AN polymer easily hydrolyzable under the subsequent hydrolytic treatment condition and the core component is made of another AN polymer which is difficult to be hydrolyzed; or sheath-core type fibers of which the sheath component is made of an easily hydrolyzable AN polymer and the core component is made of another polymer (for example, polyamide, polyolefin, etc.). In addition, so far as the fibers have a cross-sectional structure in which at least a part of an AN polymer is exposed on the surface of the fibers, such fibers can be used as starting material AN fibers of the present invention. Therefore, it does not deviate from the scope of the present invention to use as the starting material, fibers produced by particular spinning processes, such as fibers produced by random composite spinning of polymers of two or more components; so-called "sea-islands" type composite fibers; "side-by-side" bicomponent conjugated fibers; or "sandwitch" type composite fibers, etc.

The fibers thus produced can be subjected to the subsequent hydrolytic treatment whatsoever form the fibers may take, such as short fibers, long fibers, fiber tows, yarns, knitted products, woven products, or nonwoven products, etc. It goes without saying that waste fibers discharged from the AN fiber production process, etc. or semi-produced fibers during said production process (for example fibers after the heat-stretching step), can be also used as the starting material.

In order to obtain water-swellable fibers having a high degree of water-swellability and excellent physical properties from such AN fibers, it is necessary to selectively hydrogel only the outer layer of the AN fibers so that the fibers can have a multiple layer structure composed of a hydrogel outer layer and an inner layer of an AN polymer and/or another polymer.

The degree of water-swellability of the thus produced fibers having a dual or multiple structure ranges desirably from 3 to 300 cc/g and more preferably from 5 to 200 cc/g. Furthermore, in order that the fibers can have such a degree of water-swellability and retain sufficient fiber physical properties, it is desirable to control the ratio of the hydrogel outer layer to not more than 55%, based on the total volume of the fibers when dried up, and more preferably within the range of from 5 to 40%. If the ratio of the hydrogel layer exceeds the upper limit of the recommended range of the present invention, the fibers will not retain sufficient fiber physical properties, and if the ratio is less than the lower limit of the preferred range, the fibers will not exhibit a sufficient water-swellability. It is desirable that the amount of the salt-type carboxyl groups represented by the formula—COOX (wherein X is an alkali-metal or $NH_4$) should be adjusted to a value ranging from 0.1 to 4.0 m mol/g, more preferably from 0.5 to 3.5 m mol/g. If the amount of the salt-type carboxyl groups is out of the lower limit of the recommended range, the water-swellability will be insufficient, and when the amount exceeds the upper limit of said range, the fibers will have poor physical properties and will become brittle and less flexible. As regards the kind of the salt-type carboxyl groups, these may be an alkali-metal carboxylate such as Li—, Ki—, or Na—, etc. carboxylate, or $NH_4$-carboxylate, or a mixed carboxylate of two or more of these alkali-metals and $NH_4$.

A detailed explanation on the method of hydrolyzing the AN fibers will be made in the following. So far as it is possible to finally obtain water-swellable fibers consisting of a hydrogel outer layer and an inner layer of an AN polymer, there are no restrictions on the method of hydrolysis. However, in the present invention, the following means is employed which is a one-step hydrolyzing-cross-linking process that can selectively hydrogel only the outer layer of the AN fibers and can easily control the ratio of said outer layer.

Namely, there is employed either a process (hereinafter referred to as "A" process) in which an aqueous solution of an alkali-metal hydroxide in a high concentration not less than 6.0 mol/1000 g is caused to act on the AN fibers, or another process (hereinafter referred to as "B" process) in which an aqueous solution of an alkali-metal hydroxide in a low concentration coexisting with an electrolytic salt of a concentration not less than 0.5 mol/1000 g is caused to act on the AN fibers. Upon employing the A process, if an aqueous alkaline solution of a concentration less than 6.0 mol/1000 g is caused to act, the AN fibers are made hydrophilic indeed by the hydrolytic reaction but become water-soluble, and it is impossible to form a hydrogel outer layer to which the present invention is directed. The present invention can be more effectively realized by using an aqueous alkaline solution in the range of concentration of from 6.25 to 8.85 mol/1000 g, more preferably from 6.25 to 8.50 mol/1000 g. Under conditions exceeding the upper limit of the preferred range, the activity of the alkali-metal hydroxide is lowered, so that in order to increase the reaction rate, a high-temperature treatment is required, and also the treatment for the removal of remaining alkali becomes then difficult. Therefore, such conditions are not desirable from the viewpoint of practical use. Upon employing the B process, if the coexisting salt is in a low concentration less than 0.5 mol/1000 g, the AN fibers are made hydrophilic by the hydrolytic reaction indeed, but most of the fibers become water-soluble, and therefore it is impossible to form a hydrogel outer layer by the one-step process using an aqueous alkaline solution of a low concentration. The present invention can be more advantageously practiced industrially by using an aqueous solution of an alkali-metal hydroxide of a concentration of from 0.25 to 6.0 mol/1000 g, preferably 0.5 to 5.0 mol/1000 g, containing an electrolytic salt of a concentration of 1.0 mol/1000 g or higher. In this connection, the A process is described in further detail in Japanese Patent Publication No. 158423/1976 filed by the same applicant as that of the present invention.

The alkali-metal hydroxides used in the present invention include hydroxides of alkali-metals such as Na, K, Li, etc. and mixtures of such hydroxides. As the electrolytic salts, any salts can be used so far as they are stable under the alkali treatment condition. Such salts include those salts whose cationic component is an alkali-metal (such as Na, K, Li, etc.) or an alkali-earth-metal (such as Be, Mg, Ca, Ba, etc.) or another metal (such as Cu, Zn, Al, Mn, Fe, Co, Ni, etc.) or $NH_4$, and whose anionic component is an acid radical (such as hydrochlorate, sulfate, nitrate, chromate, dichromate, chlorate, hypochlorite, organic carboxylate, organic sulfonate, etc.) and mixtures of two or more of these salts. When an electrolytic salt whose cationic component is a divalent or higher valent element is used, the resulting hydrogel outer layer is liable to agglomerate or unite with each other, and furthermore the degree of swellability is lowered. Therefore, it is preferable to use a salt whose cationic component is an alkali-metal or $NH_4$. As solvents to replace water, aqueous mixed solvents composed of water and a water-miscible organic solvent such as methanol, ethanol, propanol, 2-methoxyethanol, dimethylformamide, dimethyl sulfoxide, etc. can be used so far as such mixed solvents do not dissolve the AN fibers being treated. If necessary, it is also possible to add other organic or inorganic substances.

If the AN fibers are subjected to an alkaline hydrolysis treatment under known conditions, substantially only water-soluble polymer is formed, but when the particular conditions of the A or B process recommended in the present invention are employed, hydrogel is formed in one-step and in high yields. This is extremely different from the results expected from the reaction under known conditions. Although the reaction mechanisms involved have not yet accounted for in detail, a possible supposition may be that, accompanied with the hydrolytic reaction of nitrile groups in the outer layer of the fibers, side-reactions to form intermolecular cross-linkages or intramolecular ring structures will proceed in a peculiar manner under the above-mentioned conditions.

It is impossible to fixedly prescribe the reaction conditions (including the temperature and/or treating time conditions) upon causing an aqueous alkaline solution as mentioned above to act on the AN fibers, because the preferred range of conditions is different depending upon the form of the polymer, the fine structure, such as crystallinity, of the polymer, the concentration of alkali, etc.

However, from the consideration of the fact that a higher temperature will generally increase the reaction rate and enhance the treating effect more advantageously, it is recommended that a temperature not lower than 50° C., preferably not lower than 80° C. should be used, whereby the present invention can be realized more effectively.

Also, there is no strict restriction on the amount of the aqueous alkaline solution for treating the AN fibers, but it is desirable to use at least 3 weight parts, preferably more than 4 weight parts, of said alkaline solution, based on one weight part of said fibers. Under such a condition, the contact between the fibers and the aqueous solution is facilitated, and the hydrophilating reaction and the crosslinking reaction of the present invention can proceed effectively.

As regards the methods of causing the aqueous alkaline solution to act on the AN fibers, these can be widely selected from known methods of treating a non-uniform system, such as a method wherein short fibers cut into desired lengths are suspended in the aqueous solution and are stirred with a shearing apparatus such as a screw-type stirrer, mixer, etc. or kneaded with a kneader; a method wherein continuous fibers in the form of long fibers, fiber tows, yarns, kinitted or woven fabrics, non-woven fabrics, etc. are caused to travel through said aqueous solution, in a tensioned or tension-free state; a method wherein short fibers, long fibers, etc. are put into a net-shaped container and are shaked in said aqueous solution; etc.

Upon producing fibers of a multiple structure consisting of a hydrogel outer layer and an inner layer of an AN polymer and/or another polymer by causing an aqueous alkaline solution to act on the AN fibers as mentioned above, it is important to control the volume ratio of the hydrogel outer layer and/or the amount of salt-type carboxyl groups (—COOX) contained therein which have a particularly close relation with the degree of water-swellability and physical properties of the fibers to be finally obtained. The method for controlling the volume ratio of the hydrogel outer layer and/or the amount of salt-type carboxyl groups can be varied depending on the kind of the AN fibers used, namely the composition, crystallinity, single-filament denier, etc. thereof, and/or on the condition for the hydrolytic treatment, namely the concentration of the alkali-metal hydroxide and/or the electrolytic salt, the temperature of hydrolysis, the amount of the aqueous alkaline solution relative to the amount of the fibers to be treated, the treating time, etc. and therefore it is difficult to prescribe the conditions fixedly. However, by controlling the hydrolytic treating time to not more than 40 minutes, preferably within the range of from 2 to 30 minutes, the object of the present invention can be easily attained. If fibers composed of a single component of an AN polymer are subjected to the hydrolytic treatment for a long time exceeding the recommended range of the present invention, water-swellable fibers having satisfactory physical properties cannot be obtained, because the inner layer of the AN polymer will be then completely lost, or even if it remains its amount will be little, or the border line between the outer layer and the inner layer will become unclear. Therefore, such a treatment for a long time is not desirable.

The water-swellable fibers thus obtained are washed with water to remove alkali-metal hydroxide remaining in said fibers. Thereafter, if necessary, the fibers are subjected to a treatment to change the salt-type carboxyl groups to alkali-metal salt or ammonium salt by a known method, and if desired the fibers are subjected to a drying treatment to form dry fibers.

In this way, it is possible to obtain water-swellable fibers composed of a hydrogel outer layer and an inner layer of an AN polymer and/or another polymer. To our surprise, the fibers have a water-swellability of from 3 to 300 cc/g, preferably from 5 to 200 cc/g, and besides, as regards fiber physical properties such as dry or wet strength, dry or wet elongation, knot strength, etc., the fibers can almost stand comparison with ordinary AN fibers for textile use (for example, dry-strength: 2.0 g/d or more; wet-strength: 1.5 g/d or more). In addition, since the inner layer of the fibers is composed of an AN polymer, the fibers do not show any dimensional change in lengthwise direction even in a swollen state.

Thus, it is striking advantages of the present invention that fibers with a high degree of water-swellability and excellent physical properties can be obtained from ordinary AN fibers or waste fibers discharged from the production process of such fibers, by a one-step treatment process with an aqueous alkaline solution, without requiring the use of fibers composed of a polymer of a particular composition containing a cross-linkable monomer, etc. as a copolymerization component, and that the degree of water-swellability and physical properties of the thus obtained fibers can be easily controlled by regulating the conditions of the hydrolytic treatment. It is also a marked feature that, since such water-swellable fibers are excellent in physical properties such as strength, elongation, flexibility, etc., the fibers can be handled in the same way as existing textile fibers.

The water-swellable fibers of the present invention which combine such a high degree of water-swellability with excellent physical properties, are spun or made into paper, in their single form or in mixture with existing natural, semisynthetic or synthetic fibers to produce novel textile materials or products having excellent moisture absorbing power, water absorbing power and water retaining power, which can be used as drapers, sanitary products, filter papers, materials for removing water from organic solvents which are not miscible with water, sealing materials, cation-exchanging fibers; or like existing hydrogel powder or grains, as instant sandbags, artificial soil, artificial sphagnum moss, materials for keeping warm or cold, etc.

For a better understanding of the present invention, examples are set forth in the following, but it is to be understood that the scope of the invention is by no means limited by the description of these examples, in which all percentages and parts are by weight unless otherwise indicated.

The degree of water-swellability, the amount of salt-type carboxyl groups (—COOX) and the volume ratio of the hydrogel outer layer are measured and calculated by the following methods:

(1) Degree of water-swellability

About 0.1 gram of sample fibers is immersed in pure water and is maintained at 25° C. After 24 hours, the fibers are wrapped in a nylon filter cloth (200 mesh) and the water remaining about the fibers is removed by a centrifuge (3 G×30 minutes, wherein G represents the acceleration of gravity). The weight of the sample fibers thus prepared is measured ($W_1$ g). The sample is then dried in a vacuum drier at 30° C. until it reaches a constant weight ($W_2$ g). From the above measurement results, the degree of water-swellability is calculated by the following formula. Accordingly, the present degree of water-swellability is a numerical value showing how many times of water based on the fibers' own weight can be absorbed and retained by the fibers.

$$\text{Degree of water-swellability} = \frac{W_1 - W_2}{W_2}$$

(2) Amount of —COOX groups (m mol/g)

About one gram of thoroughly dried sample fibers is weighed accurately (X g). After 200 ml water is added to this sample, an aqueous 1 N hydrochloric acid solution is added while heating to 50° C. to adjust the pH to 2. Then a titration curve is obtained in the usual way using an aqueous 0.1 N caustic soda. From this titration curve, the amount of caustic soda solution consumed by the carboxyl groups is obtained (Y cc). From the result of the above measurement, the carboxyl groups is calculated by the following formula:

Amount of —COOX groups = (0.1 Y/X)

If polyvalent cations are contained, the above formula must be corrected by obtaining the amount of these cations in the usual way.

(3) Volume ratio (V%) of hydrogel outer layer

A microscopic photograph of 20 filaments of the water-swollen sample is taken at 100 to 1000 magnifications (Z times), and from this photograph, the average value ($l_1$ mm) of the diameters of the core portion (the inner portion composed of an AN polymer and/or another polymer) is obtained. The volume ratio (V%) is calculated by the following formula:

$$V = \left\{ 1 - \left( \frac{1000 \, l_1}{Z l} \right)^2 \right\} \times 100$$

wherein 1 is the diameter (μ) of the AN fibers being treated.

EXAMPLE 1

Four parts of AN fibers (single-filament denier: 3 d; fiber length: 50 mm; inherent viscosity in dimethylformamide (DMF) at 30° C.: 1.3) composed of 90% AN and 10% methyl acrylate (MA) was immersed in 96 parts of a 30% aqueous caustic soda solution (7.5 mol/1000 g solution) and was boiled under stirring for 10 minutes. After removal of remaining alkali in the fibers by water-washing, the fibers were dried to obtain water-swellable fibers (I) which were white or pale yellow. The fibers (I) obtained were water-insoluble, contained an amount of —COONa of 2.8 m mol/g and had a degree of water-swellability of 174 cc/g. In Table 1 are shown several physical properties and the volume ratio (V) of the hydrogel outer layer of the fibers (I) together with the corresponding physical properties of the AN fibers before treatment.

TABLE 1

|  | Present invention Water-swellable fibers (I) | Reference values AN fiber before treatment |
| --- | --- | --- |
| Dry strength (g/d) | 2.6 | 3.2 |
| Dry elongation (%) | 34.0 | 40.0 |
| Wet strength (g/d) | 2.2 | 2.7 |
| Wet elongation (%) | 30.0 | 43.0 |
| Knot strength (g/d) | 2.3 | 3.0 |
| V (%) | 30 |  |

From the results in Table 1, it will be understood that the water-swellable fibers according to the present invention are maintained at a level substantially not inferior to the reference values of the AN fibers before treatment both in strengths and in elongations.

For comparative purposes, the same treatment was performed according to the above formulation except that an aqueous 10% (2.5 mol/1000 g) or 23% (5.75 mol/1000 g) caustic soda solution was used. In both cases, the AN fibers being treated were dissolved in the aqueous solution and formed a viscous solution. Thus, it was impossible to form water-swellable fibers of the present invention when an aqueous caustic soda solution of such a low concentration was used singly.

Also, the same treatment was performed according to the above formulation except that an aqueous 35% (6.25 mol/1000 g) caustic potash solution was used in place of the above caustic soda solutions. White or yellow fibers were then obtained which were substantially water-insoluble and water-swellable.

EXAMPLE 2

Five parts of AN fibers (single-filament denier: 6 d; filament length: 65 mm; inherent viscosity in DMF at 30° C.: 1.3) composed of 90% AN and 10% MA, were immersed in 95 parts of an aqueous 10% (2.5 mol/1000 g) caustic soda solution in which 20% (3.45 mol/1000 g) sodium chloride was present together, and according to the formulation in Example 1, the fibers were formed into water-swellable fibers (II). The thus obtained fibers (II) were water-insoluble, had a volume ratio (V) of the hydrogel outer layer of 25%, contained an amount of —COONa groups of 1.9 m mol/g and had a degree of water-swellability of 150 cc/g.

The same experiment as above was performed, with the only difference, however, that the hydrolytic treatment was prolonged to one hour. The thus-obtained fibers (III) contained an amount of —COONa groups of 8.6 m mol/g, and had a very high degree of water-swellability of 318 cc/g, but the fibers were extremely brittle. When the fibers in a water-swollen state were squeezed through the hand, the core portion of the AN polymer was completely lost.

EXAMPLE 3

The AN fibers described in Example 2 were treated in the same way as in Example 2 except that, in place of 20% sodium chloride, sodium nitrate was used and that the concentration of the latter salt and that of caustic soda were varied as shown in Table 2.

The water-swellability, the amount of —COONa groups and the volume ratio (V) of the hydrogel outer layer of the 10 kinds of the water-swellable fibers thus obtained (III to XII) were measured. The results are shown in Table 2.

TABLE 2

| Sample No. | Sodium nitrate concentration (mol/1000 g) | Caustic soda concentration (mol/1000 g) | Water-swellability (cc/g) | Amount of —COONa groups (m mol/g) | V (%) |
|---|---|---|---|---|---|
| III | 6.0 | 2.5 | 48 | 1.7 | 22 |
| IIII | 5.0 | 2.5 | 72 | 1.8 | |
| V | 4.0 | 5.0 | 203 | 3.5 | 40 |
| VI | 4.0 | 2.5 | 148 | 1.9 | 25 |
| VII | 4.0 | 0.75 | 55 | 0.8 | 10 |
| VIII | 4.0 | 0.25 | 1 | — | |
| IX | 3.0 | 2.5 | 151 | 1.8 | 23 |
| X | 1.0 | 1.25 | 103 | 1.5 | 20 |
| XI | 0.6 | 1.25 | 22 | 1.3 | |
| XII | 0.4 | 1.25 | 8 | 1.3 | |

The results in Table 2 shows that, when the concentration of the salt to coexist in the aqueous alkaline solution is less than the range recommended in the present invention (Sample no. XII) only fibers of a low degree of water-swellability are obtained. In this case, since a large amount of water-soluble polymer is produced, the yield of water-swellable fibers was so low that it was about 40%. In the case where the alkali concentration was extremely low (Sample no. VIII), it was impossible to obtain fibers of a desired degree of water-swellability. It is apparent from Sample nos. III, IIII, VI and IX that fibers of various degrees of water-swellability can be produced by varying the salt concentration even though the alkali concentration remains constant.

EXAMPLE 4

AN fibers (single-filament denier: 15 d; filament length: 50 mm; inherent viscosity in DMF at 30° C.: 1.5) consisting of 80% AN and 20% vinyl acetate were treated according to the formulation described in Example 1 except that the treating time was 6 minutes. Water-swellable fibers (XIII) were obtained which were white or yellow and had a degree of water-swellability of 143 cc/g.

What is claimed is:

1. Water-swellable fibers with a high degree of swellability composed of an outer layer of a hydrophilic crosslinked polymer and an inner layer of an acrylonitrile polymer, such fiber being produced by contacting acrylonitrile fibers with an aqueous solution of an alkali-metal hydroxide of a high concentration not less than 6.0 mol/1000 g, or an aqueous solution of an alkali-metal hydroxide of a low concentration coexisting with an electrolytic salt of a concentration not less than 0.5 mol/1000 g for a sufficient time to cross-link and render the outer layer of the fibers hydrophilic, thereby producing fibers having said hydrophilic cross-linked outer layer and a non-cross-linked, non-hydrophilic acrylonitrile inner layer.

2. The fibers as claimed in claim 1 having a degree of water-swellability of from 3 to 300 cc/g.

3. The fibers as claimed in claim 1 wherein the outer layer composed of a hydrophilic cross-linked polymer constitutes a volume not more than 55% based on the total volume of the fibers.

4. The fibers as claimed in claim 1 characterized by using, as the aqueous solution of an alkali-metal hydroxide of a low concentration, an aqueous solution of an alkali-metal hydroxide of a concentration of 0.25 to 6.0 mol/1000 g in which an electrolytic salt of a concentration not less than 0.5 mol/1000 g coexists.

5. The fibers as claimed in claim 1 wherein 0.1 to 4.0 m mol/g of salt-type carboxyl groups represented by —COOX, wherein x is an alkali-metal or NH4, is introduced into the fibers.

6. The fibers as claimed in claim 1 wherein as the electrolytic salt, a salt of which the cationic component is an alkali-metal or NH4, is used.

7. The fibers as claimed in claim 1 wherein an aqueous solution of an alkali-metal hydroxide is contacted within the acrylonitrile fibers at a temperature not lower than 50° C.

8. The fibers as claimed in claim 1 wherein an aqueous solution of an alkali-metal hydroxide is contacted within the acrylonitrile fibers for a time not more than 40 minutes.

9. Water-swellable fibers with a high degree of swellability of from 3 to 300 cc/g which consists essentially of an outer layer of a hydrophilic carbon-carbon covalent bonded cross-linked acrylonitrile polymer containing 0.1 to 4.0 m mol/g fiber of salt-type carboxyl groups represented by —COOX, wherein X is an alkali-metal or NH4, and an inner layer of an acrylonitrile polymer.

10. The fibers as in claim 9 wherein the outer layer composed of a hydrophilic cross-linked polymer constitutes a volume not more than 55% based on the total volume of the fibers.

* * * * *